United States Patent [19]

Lautenschläger

[11] Patent Number: 5,750,008

[45] Date of Patent: May 12, 1998

[54] METHOD AND DEVICE FOR THE EXTRACTION TREATMENT OF A SAMPLE

[76] Inventor: Werner Lautenschläger, Waldstrasse 15, D-88299 Leutkirch, Germany

[21] Appl. No.: 716,315

[22] PCT Filed: Jan. 26, 1996

[86] PCT No.: PCT/EP96/00329

§ 371 Date: Oct. 2, 1996

§ 102(e) Date: Oct. 2, 1996

[87] PCT Pub. No.: WO96/23565

PCT Pub. Date: Aug. 8, 1996

[30] Foreign Application Priority Data

Feb. 3, 1995 [DE] Germany .................. 195 03 591.7

[51] Int. Cl.[6] .................. B01D 11/00; B01D 3/00
[52] U.S. Cl. .................. 203/43; 203/73; 203/87; 202/185.1; 202/185.5; 202/185.6
[58] Field of Search .................. 203/46, 73, 87; 202/185.1, 185.5, 185.6; 422/186

[56] References Cited

U.S. PATENT DOCUMENTS

| | | | |
|---|---|---|---|
| 3,291,703 | 12/1966 | Dvonch et al. | 202/185.6 |
| 3,401,096 | 9/1968 | Wondrak | 202/185.5 |
| 4,156,631 | 5/1979 | Andrei | 202/185 |
| 4,165,360 | 8/1979 | Casper et al. | 422/202 |
| 4,581,133 | 4/1986 | Tomes | 210/90 |
| 4,749,030 | 6/1988 | Knox, Jr. | 165/111 |
| 5,382,414 | 1/1995 | Lautenshlager | 422/186 |
| 5,447,077 | 9/1995 | Lautenschlager | 73/863.11 |

*Primary Examiner*—Nina Bhat
*Attorney, Agent, or Firm*—Fitzpatrick, Cella, Harper & Scinto

[57] ABSTRACT

In a method for the extraction treatment of a sample (19) with a solvent which is liquid at normal ambient temperature and normal pressure, in which the solvent is introduced into a preferably heatable sample chamber (12a) and there brought into contact with the sample (19), in which the solvent vapour arising in the sample chamber (12a, 26) is drawn off out of the sample chamber in such a manner that an under-pressure arises in the sample chamber and a further part of the liquid solvent passes into the vapour phase, and in which the drawn off solvent vapour is cooled outside the sample chamber (12a, 26) and thereby, for the purpose of recovery of pure solvent, is at least partially passed back into the liquid phase, the drawn-off solvent vapour is additionally subjected to over-pressure.

18 Claims, 1 Drawing Sheet

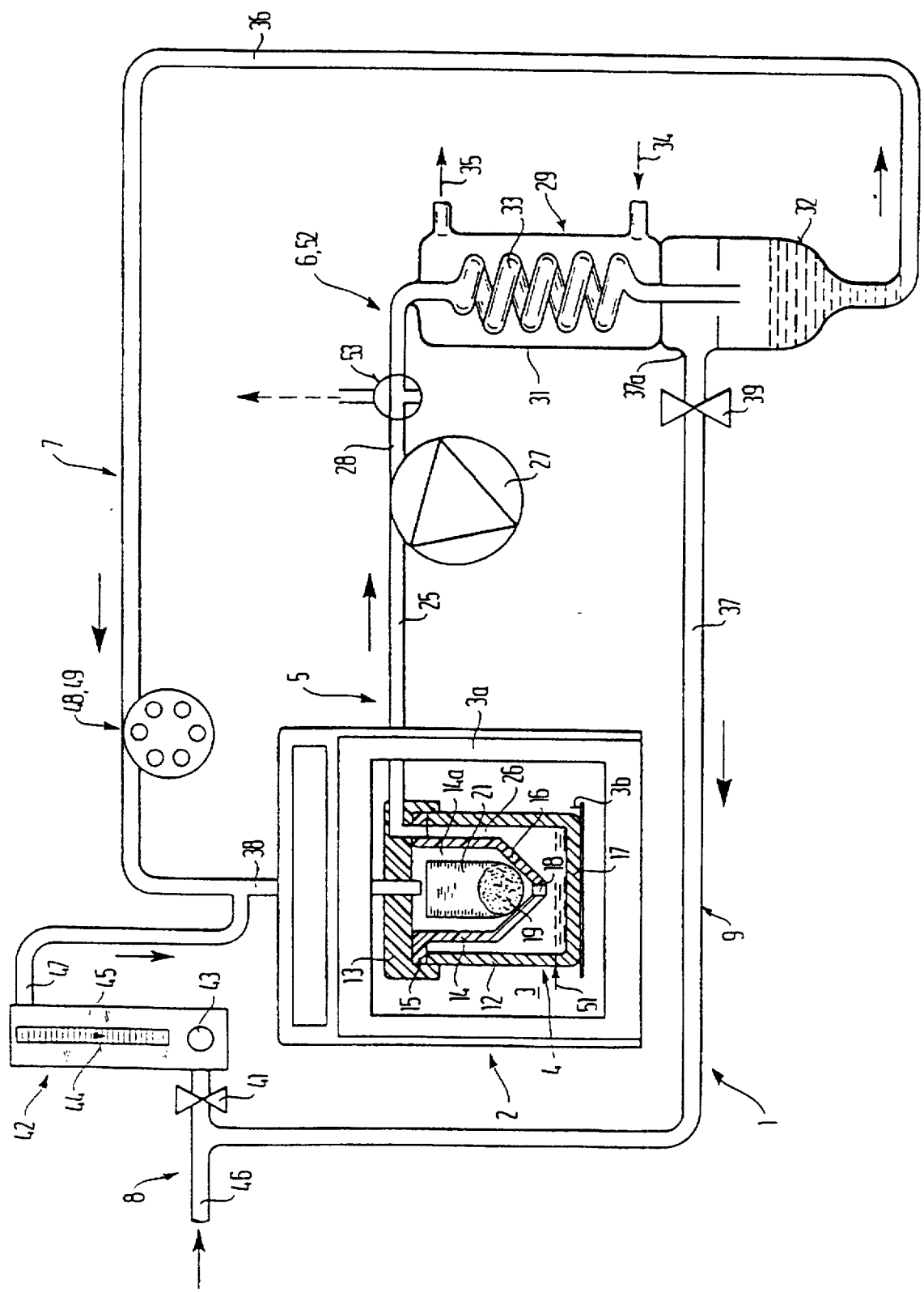

METHOD AND DEVICE FOR THE EXTRACTION TREATMENT OF A SAMPLE

FIELD OF THE INVENTION

The invention relates to the extraction treatment of liquid or in particular solid samples in which a substance is bound. This substance is to be extracted by means of the extraction treatment, i.e. dissolved out or washed out. For the extraction, a gaseous or in particular liquid solvent is used. An extraction using gas takes place for example upon the "drying" of a sample. Here, an inert gas or air serves as a transport medium for water vapour which, upon heating of the sample, is formed in the sample from the water bound in the sample.

DESCRIPTION OF THE RELATED ART

In the case of extraction in the laboratory, as a rule one works with a liquid (at normal pressure) solvent. The liquid solvent is brought into contact with the sample in a heatable chamber. The heatable chamber may be an oven heatable with microwaves. Heating is expedient or even necessary, because the substance to be extracted can as a rule be more easily dissolved out from the sample at higher temperatures and because the solvent can take up a larger quantity of the material to be extracted at higher temperatures (dissolving power increases with the temperature).

Since the solvent is expensive and in most cases toxic (poisonous), one is concerned to recover this solvent after an extraction treatment for reasons of economy and/or for the purpose of avoiding damage to the environment or to health. A known process and a known device for this purpose are described in DE 42 23 116A1. With this known process or device the heatable chamber is evacuated by means of an evacuation line leading to the outside of the heating device to a pump, whereby the gaseous solvent evacuated off is first cooled in a condensate cooler and—so far as this is possible at the evacuation under-pressure—transformed into the liquid phase before it reaches the pump. The solvent condensate recovered by these means, which is subject to under-pressure in the condensate cooler, can be brought again to normal pressure after the process has been terminated and employed again for an extraction treatment. For this purpose, it is placed into an solvent container out of which the solvent is then drawn off by a solvent pump, e.g. a tube pump, and introduced into the heatable chamber, preferably in such a manner that the solvent drips on to the sample.

With this known process or device it is important that the pump—which generates the under-pressure upon drawing off of the solvent out of the heatable chamber—is arranged after the condensate cooler in the direction of flow. Atmospheric pressure prevails at the output of the pump.

A disadvantage of this known technique consists in that the efficiency of the recovery of the solvent is low. From DE 41 14 525A1 and from the earlier patent application of the present applicant P 44 09 887.4 there can be understood in each case a process and a device for the extraction of samples whereby the extraction is effected on the one hand at an over-pressure in a pressure resistant container and on the other hand by means of a Soxhlet apparatus arranged in the pressure container, in a circulation restricted on the one hand to the interior of the pressure container and on the other hand also restricted in time. With this technique, the solvent reaches the sample, placed in a special sample container, from above, whereby the solvent enriched with the extracted substance flows through a lower through-flow or outlet of the sample container into a chamber located beneath the sample and collects there. Further, with this technique, the solvent with the substance to be extracted is moved in the internal circulation by means of the Soxhlet apparatus and is enriched with the extracted material to a large measure. Here, the solvent located beneath the sample is heated and therewith evaporated and the rising solvent vapor is condensed above the sample by means of a cooling device, whereby the vapor—again in liquid form, drops onto the sample and again dissolves out the substance to be extracted from the sample. With this known technique, an over-pressure arises in the pressure container because of the heating and the evaporation of evaporable substances contained in the sample and of the solvent. This over-pressure is a consequence of the heating which serves the purpose on the one hand of heating the sample and thereby to promote the extraction and on the other hand to evaporate the solvent in order to make the internal circulation possible. When the solvent is saturated it must be again separated from the substance dissolved therein, outside of the heatable chamber in a special process and/or be disposed of. The separation in a isolated process and the disposal are problematic in particular when the solvent is toxic. Disposal is desired also for reasons of environmental protection and economy. In particular in the case that the solvent is expensive and/or toxic, one is therefore concerned to recover the solvent in a process which is directly coupled to the extraction. Although this is possible with the technique which can be understood from DE 44 23 116A1 and the earlier patent application P 44 19 648.2, the efficiency which can be achieved thereby is slight.

SUMMARY OF THE INVENTION

Thus, the object of the invention is to provide an extraction device which ensures a recovery of the solution as immediately as possible, with simple means.

In accordance with the invention this object is achieved in that the suction pump for the solvent vapor in the heatable chamber is connected before the condensate cooler, in the direction of flow, so that in the heatable chamber under-pressure continues to prevail but increased pressure prevails in the condensate cooler. Through the increased pressure in the condensate cooler, the solvent vapor has the tendency—with constant cooling temperature—to pass over more strongly into the liquid phase, with the consequence that significantly more liquid solvent is recovered in the condensate cooler than with the known process. By these means, the efficiency is increased. The solvent can be directly delivered to the sample, preferably by means of a pump—with the omission of the solvent container, whereby an over-pressure may prevail before the pump in the direction of flow, since the pump—which may be formed as a tube pump—acts like a valve. This means that at the output of the pump, despite the transporting effect of the pump, a lower pressure can prevail than at its input. This is also necessary since the output of the pump is led into the heatable chamber containing the sample and the heatable chamber is connected with the suction line for the solvent vapor.

In contrast to this, with the above-described state of the art, the efficiency is low because under-pressure prevails in the condensate cooler, i.e. the solvent has the tendency—even at the relatively low temperatures in the cooler—largely to remain in the vapor phase because of the under-pressure. This has not only the consequence that separated solvent still cannot be fed directly again (in the manner of a closed circulation) into the extraction process (the solvent container, from which the solvent pump transports, is at normal pressure), but also the disadvantage that after the vacuum pump, connected after the condensate cooler, a gas strongly enriched with solvent vapor exits to the atmosphere. This is not acceptable at least in the case when the solvent is toxic. To counter this, one could connect after the vacuum pump a further condensate cooler working at atmospheric pressure, in which the solvent vapor still contained richly in the gas could be recovered. However, the additional outlay required therefor is significant and not desired.

In its more specific aspects, the invention involves process and device features which further improve the functioning, the capabilities, the economy and the environmental acceptability of the device and provide for simple and economically manufacturable configurations and further make possible indirect heating of the sample and/or of the solvent.

BRIEF DESCRIPTION OF THE DRAWING

Below, the invention and further advantages which can be achieved thereby will be described with reference to exemplary embodiments and the drawing which is a diagrammatic representation of an extraction/treatment device which forms a preferred embodiment of the invention.

DETAILED DESCRIPTION OF THE PREFERRED EMBODIMENT

The main parts of the device, generally designated as 1, are a heating apparatus 2, preferably working with microwave radiation, having a heating chamber 3 in a housing 3a which can be closed by means of a door or the like, at least one or preferably several sample containers 4, which can either be directly placed into the heating chamber 3 or can be placed upon a holder 3b, preferably rotatable and arranged in the heating chamber 3, having places for the sample containers 4, a suction device 5 for drawing off vapors out of the sample container or containers 4, a condensation device 6 connected after of the suction device 5 for condensing the vapor or vapors, a condensate return device 7 for returning the condensate into the sample container or containers 4, a gas delivery device 8 for delivering a flushing gas, e.g. air or an inert gas, into the sample container or containers 4, a gas return device 9, for returning remainder vapor which may be mixed with the flushing gas, and an electrical control device for controlling the device 1 and regulating the heating power. So far as several sample containers 4 are present, they are in principle the same as one another and preferably identically formed, so that only one sample container 4 will be described below. The sample container 4 consists of a pot-like or pot-shaped lower container part 12 and a lid 13 which can be placed thereon, and a pot-like or pot-shaped sample receptacle 14 which can be placed into the lower container part 12, which sample receptacle can be so supported in the lower container part 12 by means of a support part—here a flange 15 lying on an edge shoulder of the lower container part 12—that the sample receptacle is located with its floor part 16 at a spacing above the floor of the lower container part 12. The cross-sectional form and size of the receptacle 14 is so dimensioned that at least one channel, preferably a free annular space, is provided between the receptacle 14 and the lower container part 12. There is provided in the floor part 16 of the receptacle 14 a discharge opening 18, which may also be formed by means of perforations. The sample or sample material—referenced with 19—is placed from above preferably in a perforated basket 21 into the receptacle 14.

With its components, the sample container 4 consists of microwave permeable material, preferably plastics. As material there is suitable preferably polytetrafluoroethylene (PTFE/teflon) or tetrafluoro-coploymers (TFM) or also quartz, ceramics or glass. The lower container part 12, the lid 13 and/or the receptacle 14 may be of material partially absorbent for microwaves, in order to provide—when irradiated with microwaves—and indirectly effective heating in the sample container 4. For this purpose, there is preferably suited a plastics in which material parts, such as particles of microwave absorbing material, in particular graphite, are mixed or alloyed. One such plastics is known per se under the designation Weflon.

Otherwise, the heating apparatus 2 and/or the sample container or containers 4 may be of the configuration which can be understood from DE 42 23 116 A1 or from the earlier patent application P 44 19 648.2. In order to avoid repetition, reference is made to these configurations to the fullest extent.

The suction device 5 includes a suction line 25 which extends from the upper region of the free space or collection space 26 between the lower container part 12 and the receptacle 14 to a pump 27 arranged outside the heating chamber 3, and thereby preferably penetrates the lid 13 in a sealed manner after previously passing through the flange 15 and then crossing the heating chamber 3 and the housing 3a of the heating apparatus 2 surrounding the heating chamber 3. The pump 27 is preferably of resistant material, in particular plastics, e.g. PTFE, and it is arranged between the suction line 25 and an onward delivery line 28, whereby the pump is such a pump that is capable of generating in the suction line 25 an under-pressure e.g. 0 to 1000 mbar and of generating an over-pressure in the onward delivery line 28. The onward delivery line 28 extends to a condensate cooler 29 having a cooler housing 31 and a condensate collection housing 32 arranged in its lower region. The onward delivery line 28 extends in the cooler housing 31 in the form of a cooling coil, here a cooling helix 31, preferably from the top downwards, whereby the onward delivery line 28 discharges freely into the collection chamber 32. A supply line 34 and a discharge line 35 for a preferably liquid cooling medium, such as e.g. water, is connected to the cooler housing 31. The condensate cooler 29 is preferably in principle or identically of the construction and function described in DE-GM (German Utility Model) 93 11 578 of the present applicant. Reference is made thereto to the fullest extent.

From the lower region of the condensate collector housing 32 there extends a return line 36, as part of the condensate return device 7, into the sample receptacle 14, in particular from above, whereby it passes through the housing 3a, the heating chamber 3 and the lid 13 and opens in particular centrally into the free space 14a of the receptacle 14.

From the upper region of the condensate collection housing 32 there extends a second return line 37 from a line connection 30a, as part of the gas return device 9, into the free space 14a of the receptacle 14, whereby preferably the return line 36 and the return line 37 are brought together, in particular before the housing 3a, to a common return and delivery line 38, which opens in the above-described manner into the receiving space 14a of the receptacle 14. In the return line 37, there is preferably in its initial region a pressure reduction or over-pressure valve 39 and in its further extent a valve 41 and a flow quantity measurement device 42, in particular having a float body 43 (ball) and a scale 44 behind a transparent wall 45. Before or after the valve 41, a supply line 46 is connected as part of the gas supply device 8 to the return line 37. The common onward delivery line 47 opens into the common return line 38 which is at the same time the supply line for the gas supplied through the supply line 46.

The condensate return device 7 has a preferably adjustable component as choke 48 in the form of a valve or preferably a pump, in particular a tube pump 49, which is arranged in the vicinity of the end of the return line 36 preferably outside of the housing 3a and before the connection point with the line 47, in the return line 36. Because of the presence of the choke 48, the pump 27 generates at the output side an over-pressure which is greater than 1 bar, preferably 1.5 to 10 bar. This pressure is determined by the power of the pump 27 and the size of the choke cross-section of the choke 48 and the power of the pump 49, which are to be correspondingly dimensioned.

The above-described controllable functional parts of the device 1 are connected with the control device 11 by means of control or signal lines. There may belong thereto also a temperature measurement device 51 at the sample container 4, whereby a control or regulation device for the heating power functions such that when a particular temperature in the sample container 4 is exceeded heating power is switched off and when a particular temperature is undershot is again switched on, or—taking into consideration a desired temperature and the actual temperature in each case—the heating power is regulated in known manner.

In operation of device 1, the heating apparatus 2 is switched on and a suitable solvent—liquid at normal pressure—is supplied through the common return line 38, which solvent drips onto the sample 19 dissolves out the substance to be extracted and flows down with the substance into the collection chamber 26, in which it evaporates. The solvent vapor is drawn off by means of the suction line 25, is cooled in the pressure condensation system generally designated by 53, and condensed, and returned through the return line 36 into the sample container 4 in circulation.

After switching off of the condensate return device 7 and, if appropriate, switching off of the gas return line 37, the device can be employed also for the drying of samples 19 or for drying before or after an extraction as described above, with maintenance of the function of the gas supply device 8 and, if appropriate, of the gas return device 8. In the drying process, wet vapors, in particular water vapours, are drawn off, preferably condensed and discharged.

The or a particular signal of the flow quantity measurement device 42 can be employed for the purpose of indicating, in particular when drying, that the evaporation process has ended, whereby the heating can be switched off.

With the configuration in accordance with the invention, the solvent vapor drawn off from the sample container 4 still does not completely condense in the condensate cooler 29. Therefore, at the output of the cooler 29 there is provided the over-pressure valve 39 which allows the emission of solvent vapor out of the cooler 29 when a particular pressure is exceeded. In the return line 37 or common onward delivery line 47 the solvent vapor may be under normal pressure due to the connection with the air supply or a gas, in particular inert gas, source. Thereby, relative to the cooler 29, the solvent vapor in the return line 37 can after the condensation expand to a large degree, with the consequence that the density of the solvent vapor molecules in this line is extremely slight. The gas is correspondingly to be considered as "dry". This is important because it can be employed for the drying process for the sample. With the drying process the valve 41—having a preferably adjustable through-flow cross-section—is opened, i.e. inert flushing gas at atmospheric pressure is supplied to the heatable chamber and the sample located therein, which flushing gas is provided with small quantities of solvent vapor. Normal pressure then prevails in the sample container 4. At the same time, upon drying, the solvent pump 49 should be (but need not be) stopped to prevent recirculation of solvent. With the drying process which is described in the earlier application P 44 19 648.2 in particular at page 18, 4th paragraph, the sample is heated and the water vapor arising upon the heating of the sample is flushed out of the sample by means of the flushing gas and drawn off. If the water vapor is to be separated from the solvent, this can be effected by means of an outlet through the line 46. The water vapor is then issued to the environment (which is not environmentally damaging). Thus, the drying is here effected with a pressure in the sample container 4 tending towards normal pressure. However, the solvent pump 49 still provides for an under-pressure—if only a lesser under-pressure—in the sample container 4.

When little water vapor is issued from the sample 19 the connection to the environment by means of the line 46 can be closed. The enrichment of the solvent with water is, in this case, negligibly small. At the same time, however, due to the stronger under-pressure (vacuum) in the sample container 4, the efficiency upon drying is substantially increased.

The device 1 thus includes a closed circulation for the solvent extraction from the pressure condensation system 52. Due to the under-pressure in the sample container 4 (0 to about 1000 mbar) there is attained a rapid vacuum evaporation of the solvent, whereby the solvent vapor is densified with the corrosion resistant pump 27. By these means, the boiling point is increased and a substantially higher vapor concentration and yield is attained. With one dose (defined quantity) of solvent, extraction can take place as often as desired, whereby the peristatic pump 49 can act as a dosing device for a particular dose for the solvent supply directly effective in the circulation. The pump 49 or also choke 48 is to be correspondingly controlled. By these means, a too large supply quantity or an overflow of the solvent supply is precluded. During the extraction, the under-pressure, e.g. 100 to 300 mbar, can be regulated up to normal air pressure, ca. 1000 mbar. The pressure on the condensation side remains constant due to the effect of the over-pressure valve 39. During the extraction process, with the under-pressure generated in the sample container 4, or also at normal pressure, there is attained an improved extraction effect due to the heating (improved solubility in the hot solvent), since higher solvent temperature can be attained. Thereby, the higher of the solvent has a greater dissolving power as a consequence. The heating of non-polar solvents by the microwave irradiation is ensure by means of a receptacle 14 and/or a lower container part 12 of material which is partially microwave absorbent, as has already been described.

In the drying process, the constant supply of the moisture—and solvent—dry expansion gas, which arises after the over-pressure valve 39 and is brought to the inlet side into the sample container 4 offers a further advantage. The "dry" gas provides an improved drying efficiency through gas extraction (flushing with dry gas). With the aid of the gas flow measurement and regulation unit 42 the under-pressure can be definedly set by means of the corresponding control or regulation of the heating, whereby through pressure drop the evaporation end point can also be determined, when no further solvent is evaporated, or the concentration of the solvent vapor falls.

With samples 19 having a high portion of water or undesired solvents, the vapor in the flow in can be channelled by means of a switchable branch-off, e.g. a two-way valve 53, for separation, whereby an undesired mixing is avoided.

With the presence of several sample containers 4, by means of corresponding multiple channel pumps 27, 49 the sample containers 4 present can be simultaneously evacuated and charged with solvent.

Within the scope of the invention it is possible, by means of the employment of several pumps 27 and respective condensate coolers 29 connected therebetween, to improve the efficiency even with difficult solvents and easily condensable gases, such as e.g. $CO_2/N_2O$ or the like, up to approaching 100%.

Within the scope of the invention, the return by means of the return line 37 and/or the return of the solvent condensate by means of the return line 36 are advantageous also in the case of condensation without over-pressure. For this reason, these returns or the configuration making these returns possible, are to be attributed their own inventive significance.

I claim:

1. Method for the extraction treatment of a sample with a solvent which is liquid at normal ambient temperature and normal pressure, said method comprising the steps of:

introducing the solvent into a sample chamber and there bringing the solvent into contact with the sample whereby a portion of the solvent evaporates;

drawing off the solvent vapor which arises in the sample chamber in such a manner as to produce a vacuum in the sample chamber, whereby a further part of the liquid solvent passes into the vapor phase;

subjecting the drawn-off solvent to a positive pressure; and cooling and liquefying at least a portion of the drawn off and pressurized solvent vapor to recover pure solvent.

2. A method according to claim 1, further comprising the steps of:

supplying the solvent in a dosed manner, or; and introducing the recovered solvent directly back into the solvent chamber, without intermediate storing, in such a manner that a closed solvent circulation arises.

3. A method according to claim 1, further including the steps of:

expanding the solvent still remaining in the vapor phase, after it has been cooled and subjected to a positive pressure, to lower pressure; and delivering said solvent back to the sample chamber.

4. A method according to claim 3, further comprising the step of:

in the expansion of the solvent vapor to higher pressure, at least partially interrupting the solvent supply and;

extracting vapors which have formed in the sample and issued therefrom.

5. A device for carrying out the extraction treatment of a sample with a solvent which is liquid at normal ambient temperature and normal pressure, in which the solvent is introduced into a sample chamber and there brought into contact with the sample, in which solvent vapor arising in the sample chamber is drawn off out of the sample chamber in such a manner that a vacuum arises in the sample chamber and a further part of the liquid solvent passes into the vapor phase, and in which the drawn off solvent vapor is cooled outside the sample chamber and thereby, for the purpose of recovery of pure solvent, is at least partially passed back into the liquid phase, said apparatus comprising:

an apparatus housing with a hollow, chamber into which the sample can be brought;

a supply line opening into the sample chamber for the supply of a solvent which is liquid at normal pressure and at normal ambient temperature;

a component with a valve effect connected in the supply line;

a suction line connected with the sample chamber;

a condensate cooler connected to the suction line; and a suction pump arranged in said suction line for drawing off solvent vapor arising in the sample chamber and for generating a vacuum in the sample chamber, which promotes the passage of liquid solvent into the vapor phase;

said suction pump being capable of generating a positive pressure at its output and being connected in the suction line between the sample chamber and the condensate cooler, the input of the suction pump being connected with the sample chamber and its output being connected with the condensate cooler.

6. A device according to claim 5, wherein those parts of the suction pump which come into contact with the solvent are of inert material.

7. A device according to claim 5, wherein:

a collection container of the condensate cooler is connected via a connection line with said supply line;

and wherein a component having a valve effect is connected in the connection line.

8. A device according to claim 7, wherein the component having a valve effect is a tube pump.

9. A device according to claim 7, wherein;

the collection container of the condensate cooler is provided with a gas output connection for solvent still remaining in the vapor phase, wherein;

a gas output connection from the condensate cooler is connected via a flow-off line with said supply line with the sample chamber, and wherein;

a pressure reduction valve is connected in the flow-off line.

10. A device according to claim 9, wherein;

the pressure reduction valve is an over-pressure valve which responds when the pressure in the condensate cooler exceeds a predetermined maximum pressure.

11. A device according to claim 9, wherein;

the flow-off line downstream of the pressure reduction valve, in the direction of flow of the solvent vapor, is open to an inert gas, source.

12. A device according to claim 11, wherein;

the flow-off line contains, downstream, in the direction of flow of the solvent vapor, of the point at which the flow-off line is open to an inert gas source, a further valve having variable through-flow cross-section.

13. A device according to claim 5, wherein;

a valve is connected in said suction line between said suction pump and said condensate cooler.

14. A device according to claim 5, wherein;

the line extending between the suction pump and the condensate cooler continues as a cooling coil into a cooler housing through which a cooling medium can flow.

15. A device according to claim 5, wherein;

said housing has a heating chamber; and wherein the sample chamber is arranged in a sample container which is connectable with said suction line and with said supply line.

16. A device according to claim 15, wherein;

the sample container has a pot-shaped lower container part, a seal lid which can be placed thereupon, and a receptacle for a sample which can be placed into the lower container part; and wherein there is arranged between the lower container part and the receptacle a collection space for solvent which extends toward the upper edge of the lower container part, said collection space being in communication with the suction line.

17. A device according to claim 16, wherein;

the suction line and the supply line extend through the lid.

18. A device according to claim 17, wherein;

at least one of the lower container part, the lid and the receptacle is of material partially absorbent for microwaves.

* * * * *